(12) United States Patent
Pocock et al.

(10) Patent No.: US 8,408,201 B2
(45) Date of Patent: Apr. 2, 2013

(54) FLUID PRODUCT DISPENSING DEVICE

(75) Inventors: Andrew Pocock, Cambridgeshire (GB); Stuart Kay, Cambridgeshire (GB); Paul Greenhalgh, Cambridgeshire (GB); Wayne O'Hara, Cambridgeshire (GB)

(73) Assignee: Aptar France SAS, Le Neubourg (FR)

( * ) Notice: Subject to any disclaimer, the term of this patent is extended or adjusted under 35 U.S.C. 154(b) by 935 days.

(21) Appl. No.: 12/517,912

(22) PCT Filed: Dec. 10, 2007

(86) PCT No.: PCT/FR2007/052466
§ 371 (c)(1),
(2), (4) Date: Jun. 5, 2009

(87) PCT Pub. No.: WO2008/078032
PCT Pub. Date: Jul. 3, 2008

(65) Prior Publication Data
US 2010/0288278 A1 Nov. 18, 2010

(30) Foreign Application Priority Data
Dec. 11, 2006 (FR) ..................................... 06 55406

(51) Int. Cl.
*A61M 15/00* (2006.01)
*A61M 16/00* (2006.01)
(52) U.S. Cl. .................................................. 128/203.21
(58) Field of Classification Search ............. 128/200.14, 128/200.23, 203.15, 203.19, 203.21
See application file for complete search history.

(56) References Cited

U.S. PATENT DOCUMENTS

| 6,880,722 | B2* | 4/2005 | Anderson et al. ................ 221/71 |
| 2004/0244794 | A1* | 12/2004 | Richards .................. 128/203.15 |
| 2005/0005934 | A1* | 1/2005 | Harvey ..................... 128/203.15 |
| 2005/0081853 | A1* | 4/2005 | Young et al. ............. 128/203.21 |
| 2006/0196504 | A1* | 9/2006 | Augustyn et al. ........ 128/203.15 |
| 2007/0062525 | A1* | 3/2007 | Bonney et al. ........... 128/203.21 |
| 2011/0073106 | A1* | 3/2011 | Harmer et al. ........... 128/200.23 |
| 2011/0132358 | A1* | 6/2011 | Eason et al. ............. 128/203.21 |

FOREIGN PATENT DOCUMENTS

| WO | 01/26720 A1 | 4/2001 |
| WO | 02/36189 A1 | 5/2002 |
| WO | 03/061743 A1 | 7/2003 |

* cited by examiner

*Primary Examiner* — Kristen Matter
(74) *Attorney, Agent, or Firm* — Sughrue Mion, PLLC

(57) ABSTRACT

A fluid dispenser device including a body (10) with a dispenser orifice (1), a plurality of reservoirs (21) on a strip (20) that includes a leading end (25) and a trailing end (28), a reservoir-opening mechanism (30) adapted to open a respective reservoir upon actuation, and a drive mechanism (40) for the strip (20) and bring a reservoir into register with the opening mechanism. A movable wall (500; 600, 601) separates a storage housing (11) for the elongate strip (20) from a reception housing (15), the elongate strip (20) disposed mainly in the storage housing (11) before the device is used and displaced progressively in the reception housing (15) during use. The movable wall (500) causes the volume of the storage housing (11) to decrease progressively, and the volume of the reception housing (15) to increase progressively.

10 Claims, 5 Drawing Sheets

FLUID PRODUCT DISPENSING DEVICE

FIELD OF INVENTION

The present invention relates to a fluid dispenser device, and more particularly to a dry-powder inhaler.

BACKGROUND

Inhalers are well known in the prior art. Various types exist. A first type of inhaler contains a reservoir receiving many doses of powder, the inhaler being provided with metering means making it possible, on each actuation, to remove one dose of said powder from the reservoir, so as to bring said dose into an expulsion duct in order to be dispensed to the user. Inhalers including individual reservoirs, such as capsules, that are loaded into the inhaler just before said inhaler is used are also described in the prior art. The advantage of such devices is that it is not necessary to store all of the doses inside the appliance, such that said appliance can be compact. However, the inhaler is more difficult to use, since the user is obliged to load a capsule into the inhaler before each use. Another type of inhaler consists in packaging the doses of powder in individual predosed reservoirs, then in opening one of the reservoirs each time the inhaler is actuated. That implementation seals the powder more effectively since each dose is opened only when it is about to be expelled. In order to make such individual reservoirs, various techniques have already been proposed, such as an elongate blister strip or blisters disposed on a rotary circular disk. All existing types of inhalers, including those described above, present both advantages and drawbacks associated with their structures and with their types of operation. Thus, with certain inhalers, there is the problem of accuracy and of reproducibility for the dose on each actuation. In addition, the effectiveness of the dispensing, i.e. the fraction of the dose that effectively penetrates into the user's lungs in order to have a beneficial therapeutic effect, is also a problem that exists with a certain number of inhalers. A solution for solving that specific problem has been to synchronize the expulsion of the dose with the inhalation of the patient. Once again, that can create drawbacks, in particular in that type of device, the dose is generally loaded into an expulsion duct before inhalation, then expulsion is synchronized with inhalation. That means that if the user drops, shakes, or manipulates the inhaler in an undesirable or inappropriate manner between the moment when the user loads the dose (either from a multidose reservoir or from an individual reservoir) and the moment when the user inhales, then the user risks losing all or part of the dose, with said dose possibly being spread about inside the appliance. In that event, there can exist a high risk of overdosing the next time the device is used. The user who realizes that the dose is not complete will load a new dose into the appliance, and while the new dose is being inhaled, a fraction of the previous dose that was lost in the appliance could thus be expelled at the same time as the new dose, thereby causing an overdose. In the treatments envisaged, such overdosing can be very harmful, and the authorities in all countries are issuing ever-stricter requirements to limit the risk of overdosing as much as possible. With regard to opening the individual reservoirs, it has been proposed to peel off or to unstick the closure layer. That presents the drawback of difficulty in controlling the forces to be applied in order to guarantee complete opening, without running the risk of opening the next reservoir, particularly if the opening means need to be actuated by inhalation. Another problem that exists with inhalers including a blister strip relates to the storage of the strip, in particular of the strip portion including the empty reservoirs, a difficulty being in avoiding the risk of the strip blocking, without significantly increasing the dimensions of the device.

CERTAIN OBJECTS OF THE INVENTION

An object of the present invention is to provide a fluid dispenser device, in particular a dry-powder inhaler, that does not have the above-mentioned drawbacks.

In particular, an object of the present invention is to provide such an inhaler that is simple and inexpensive to manufacture and to assemble, that is reliable in use, guaranteeing metering accuracy and metering reproducibility on each actuation, providing an optimum yield with regard to the effectiveness of the treatment, by making it possible to dispense a substantial fraction of the dose to the zones to be treated, in particular the lungs, avoiding, in safe and effective manner, any risk of overdosing, and that is as compact as possible, while guaranteeing sealing and absolute integrity of all of the doses up to their expulsion.

Another object of the present invention is to provide such an inhaler including a blister strip, in which the risk of the blister strip blocking is minimized.

Another object of the present invention is to provide such an inhaler including a blister strip, in which storage of the strip portion including the empty reservoirs is improved.

The present invention thus provides a fluid dispenser device including a body that is provided with a dispenser orifice, said body containing a plurality of reservoirs formed on a common substrate formed by an elongate strip that includes a leading end and a trailing end, the device further including reservoir-opening means that are adapted to open a respective reservoir each time the device is actuated, and drive means for driving the elongate strip, so as to bring a full reservoir into register with said opening means before and/or during and/or after each actuation of the device, the device including at least one movable wall that separates, at least in part, a storage housing for storing the elongate strip from a reception housing for receiving the elongate strip, said elongate strip being disposed, in particular rolled up in a roll, mainly in said storage housing before the device is used for the first time, and being displaced progressively in said reception housing each time the device is actuated, said at least one movable wall causing the volume of the storage housing to decrease progressively, and the volume of the reception housing to increase progressively.

Advantageously, said device includes a single movable wall that is displaceable mainly in translation.

Advantageously, said wall that moves in translation presents two concave longitudinal surfaces that face the storage housing and the reception housing respectively.

Advantageously, said movable wall includes two lateral slide surfaces that are adapted to slide against respective guide walls of said device.

Advantageously, at least one of said lateral surfaces of the movable wall and at least one of said guide walls of the device are curved, at least in part, such that said movable wall turns a little on itself during its successive movements in translation.

Advantageously, said device includes at least one movable wall that pivots.

Advantageously, said device includes a single pivot wall.

Advantageously, said pivot wall is concave relative to the reception housing.

Advantageously, said device includes two pivot walls one of which is concave relative to the reception housing and the other one of which is concave relative to the storage housing.

Advantageously, said two pivot walls slide one against the other on each pivot.

Advantageously, said elongate strip is disposed in a cassette that defines said storage and reception housing and that incorporates said at least one movable wall.

Advantageously, said at least one movable wall is displaced under the effect of thrust exerted thereon by the blister strip.

Advantageously, said opening means comprise a needle that does not move relative to the body, a reservoir being displaced against said needle each time the device is actuated, said needle penetrating inside said reservoir so as to empty it by means of an inhalation flow.

Advantageously, said opening means are actuated by the user inhaling, such that the reservoir is opened and emptied simultaneously by said inhalation flow.

BRIEF DESCRIPTION OF FIGURES

These characteristics and advantages and others of the present invention appear more clearly from the following detailed description, given by way of non-limiting example, and with reference to the accompanying drawings, in which.

DETAILED DESCRIPTION OF VARIOUS EMBODIMENTS

Figure 1:
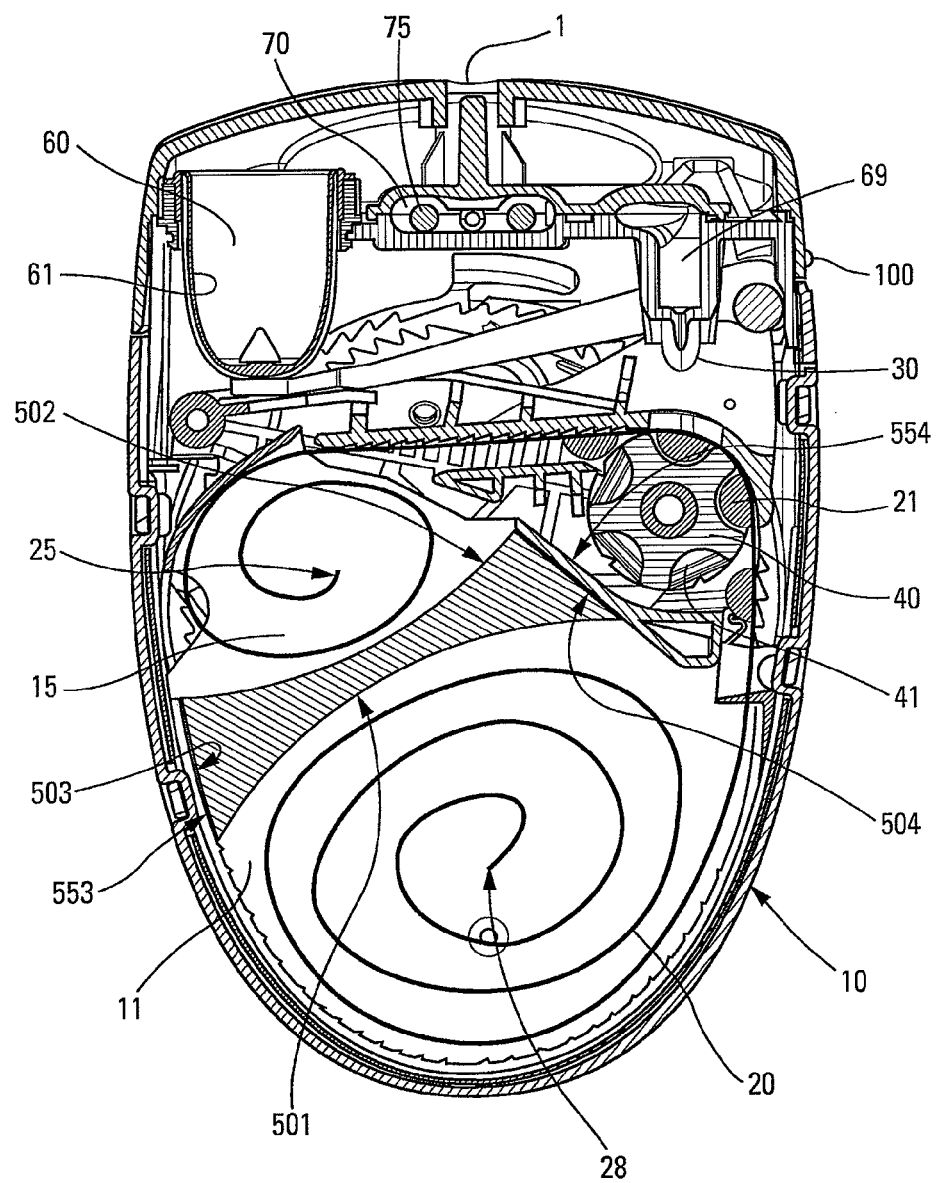
FIG. 1 is a diagrammatic section view showing a dispenser device constituting an advantageous embodiment, at the beginning of use of the device.
Figure 2:
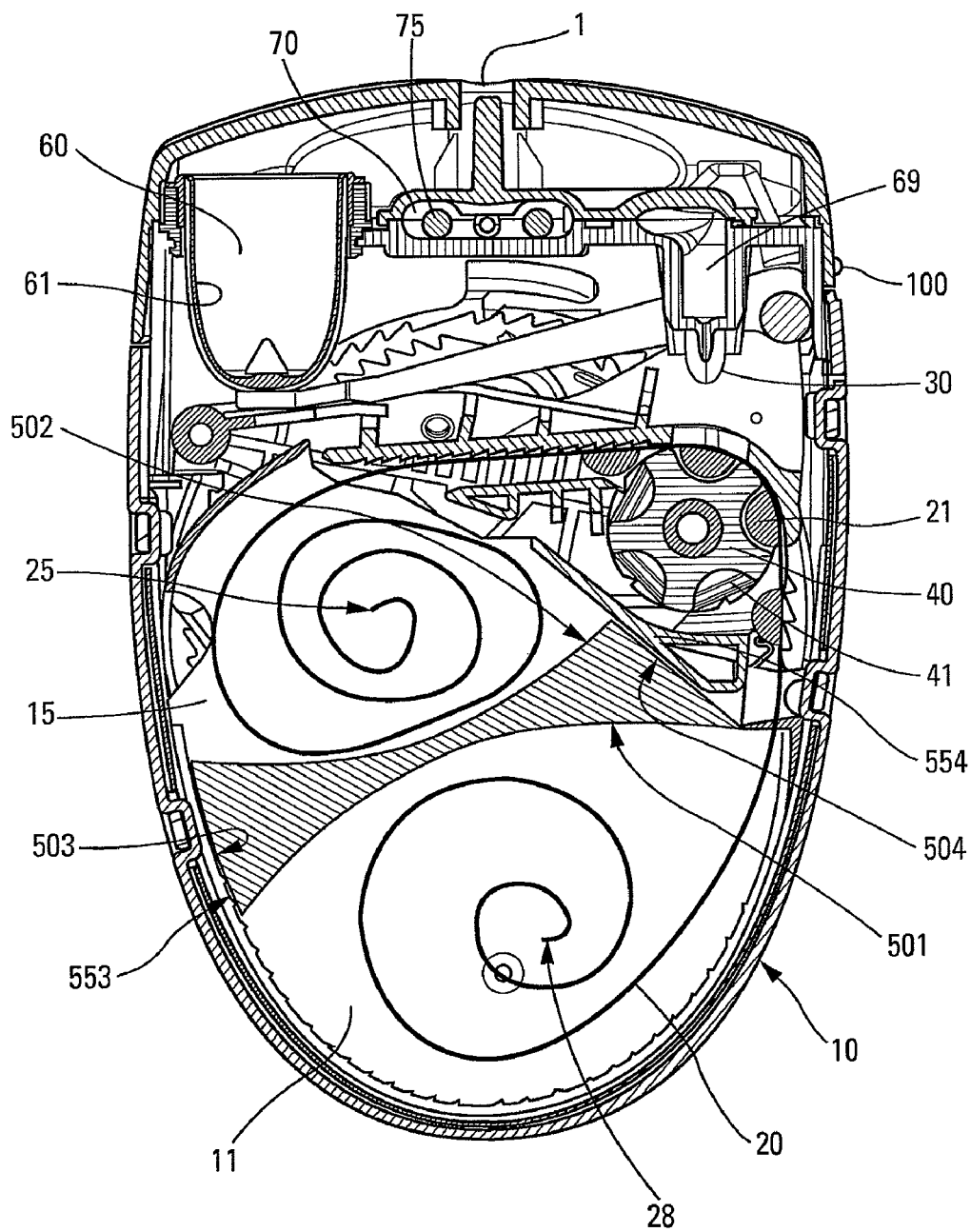
FIG. 2 is a view similar to the view in FIG. 1, at the end of use of the device.

FIGS. 1 and 2 show a first advantageous embodiment of a dry-powder inhaler. The inhaler includes a body 10 on which there can be slidably mounted one or two cover-forming portions (not shown) that are adapted to be opened so as to open and prime the device. The body 10 can be of approximately rounded shape as shown in the figures, but it could have any other appropriate shape. The body 10 includes a mouthpiece or inhaler endpiece 1 that defines a dispenser orifice through which the user inhales while the device is being actuated. The cover can open by pivoting about a common pivot axis, but any other means of opening the device can be envisaged.

The device contains a plurality of individual reservoirs 21, also known as blisters, that are disposed on a common substrate formed by an elongate strip 20 on which the blisters 21 are disposed one behind the other in known manner, the strip including a leading end 25 and a trailing end 28. The blisters 21 are not shown along the entire strip 20, so as to simplify the drawing for the purpose of clarity. The blister strip 20 is advantageously constituted by a base layer or wall that forms the cavities 21 that receive the doses of powder, and by a closure layer or wall that closes each of said blisters 21 in leaktight manner. Before first use, the blister strip 20 is rolled-up inside the body 10, preferably in a storage housing 11, and strip drive means 40 are provided for progressively unrolling the blister strip and for bringing an individual reservoir or respective blister 21 into a dispensing position each time the device is actuated. The strip portion 25 including the empty reservoirs is adapted to be rolled up in another location of said body 10, preferably a reception housing 15, as described in greater detail below.

The inhaler includes reservoir-opening means comprising a perforator system 30 for perforating the closure layer of the blisters. For example, the reservoir-opening means advantageously comprise a perforator element or a needle that preferably does not move relative to the body 10, and against which a respective blister 21 is displaced on each actuation. The blister 21 is thus perforated by said needle that penetrates into said blister so as to expel the powder by means of the user inhaling.

Displacement means 40 are also provided in the device and are adapted to displace the blister strip 20 before and/or during and/or after each actuation of the device. Advantageously, the displacement means 40 are also adapted to displace the reservoir 21 to be emptied against said perforator system 30 during actuation. The displacement means 40 can be urged by a resilient element, such as a spring or any other equivalent resilient element, said resilient element possibly being preprimed while the device is being opened. The displacement means 40 preferably comprise an indexer wheel 40 that receives and guides the blisters. Turning the wheel 40 causes the blister strip 20 to advance. In a particular angular position, a given reservoir 21 is always in a position to be opened by the opening means 30. Advantageously, rotary positioning means of said indexer wheel 40 can be provided for precisely determining its angular position after each turn. In an advantageous variant, the positioning means can comprise a projection or finger having an end that co-operates elastically with notches provided around said wheel 40. A complementary wheel could possibly be provided so as to held to guide and/or to drive the blister strip 20.

An actuation cycle of the device could be as follows. During opening of the device, the two cover-forming lateral portions are moved away from each other by pivoting about the body so as to open the device and thus prime the device. In this position, the indexer wheel 40 cannot be displaced towards the needle 30 since it is retained by appropriate blocking means 100. It is while the user is inhaling through the mouthpiece 1 that the blocking means are unblocked, thereby causing said indexer wheel 40 to be displaced towards the needle, and thus causing a reservoir 21 to be opened.

In the embodiment shown, the reservoir 21 is displaced towards its open position so as to be opened by the needle that does not move relative to the body. However, it can be envisaged that the needle can also be movable during the stage of opening the reservoir 21. For example, the needle could be displaced towards the reservoir 21 while the reservoir 21 is displaced towards the needle. In another variant, it is also possible to envisage that the reservoir 21 and the needle are displaced in the same direction during actuation, the reservoir 21 being displaced quicker in said direction, such that it comes into contact with the needle so as to be opened.

As explained above, it is desirable for the opening means to be actuated by the user inhaling. In order to trigger the reservoir opening means by inhalation, an inhalation trigger system can be provided that advantageously comprises a unit 60 that is displaceable and/or deformable under the effect of inhalation, the unit 60 being adapted to release the blocking means 100. The unit 60 advantageously comprises a deformable air chamber 61. The inhalation by the user causes said deformable air chamber 61 to deform, thereby enabling said blocking means 100 to be released, and thus enabling the indexer wheel 40 and a respective reservoir 21 to be displaced towards its opening position. The reservoir 21 is thus opened only at the moment of inhalation, so that it is emptied simultaneously. Thus, there is no risk of any of the dose being lost between opening the reservoir and emptying it.

In a variant, other inhalation trigger means could also be used, e.g. using a pivotable valve flap that, while the user is inhaling, pivots under the effect of the suction created by the inhalation, with pivoting of the valve flap causing the blocking means blocking the movable support means to be released, thereby causing the reservoir to be displaced towards the opening means.

The inhaler further includes a dispenser chamber 70 for receiving the dose of powder after a respective reservoir 21 has been opened. The dispenser chamber 70 is advantageously provided with at least one bead 75 that is displaced inside said chamber 70 during inhalation so as to improve dispensing of the air and powder mixture after a reservoir 21 has been opened, in order to increase the effectiveness of the device.

It can be advantageous for the opening system 30, in particular the needle, to be formed directly on said dispenser chamber 70, e.g. at the end of a channel 69 leading to said chamber 70.

After inhalation, when the user closes the device, all of the components return to their initial rest position. The device is thus ready for a new cycle of use.

In an aspect of the invention, the individual reservoirs or blisters 21 are formed on an elongate strip 20 that, initially, is mainly stored in the form of a roll in a storage housing 11 inside the body 10 of the device. Advantageously, the rolled-up blister strip 20 can be held by internal walls of said storage housing 11 without its trailing end 28 (in the direction of displacement of the blister strip 20) being fastened relative to said body 10, thereby making it easier to assemble the blister-strip roll inside the device. The blister strip 20 is displaced by the user, advantageously by means of the indexer wheel 40 that advantageously presents at least one, and preferably a plurality of recesses 41, having a shape that corresponds to the shape of the blisters. Thus, when the indexer wheel 40 turns, it advances the blister strip 20. No other drive system is necessary for displacing the blister strip 20 during each actuation. Naturally, in a variant or in additional manner, it is possible to use other means for advancing the blister strip, e.g. providing a profile on the longitudinal lateral edges of the blister strip, said profile being adapted to co-operate with appropriate drive means. In addition, holes formed along the lateral edges of the blister strip could also be used to cause the blister strip to advance by means of toothed wheels co-operating with said holes.

After opening one or more blisters, the blister-strip portion with the empty reservoirs must be suitable for being stored in easy and compact manner in the device. Advantageously, the used blister strip is rolled-up automatically, once again forming a roll. The leading end 25 of the blister strip 20 can possibly roll up around a rotary or stationary receiver element (not shown).

Figure 5:
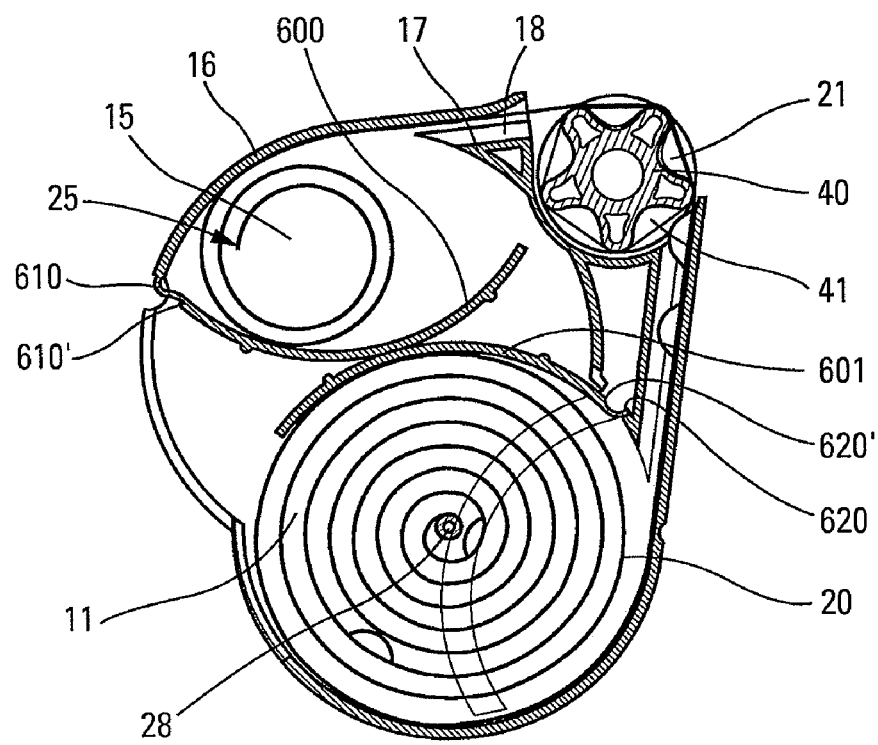
FIGS. 5 and 6 are diagrammatic section views of a dispenser device constituting yet another advantageous embodiment of the invention, respectively at the beginning and at the end of use of the device.
Figure 6:
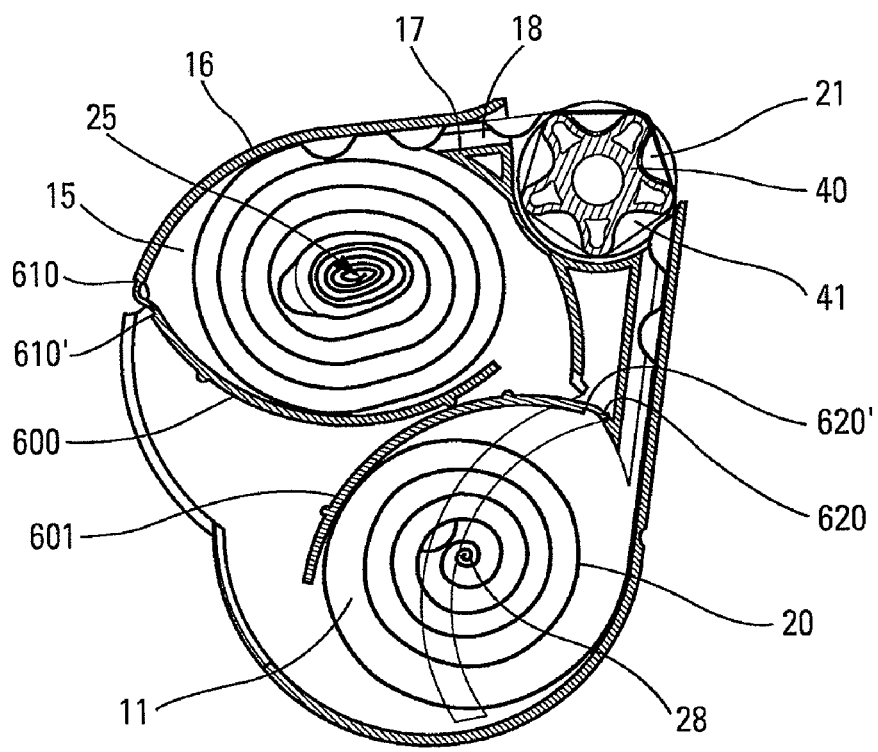

Advantageously, as shown in FIGS. 5 and 6, the reception housing 15 can include guide walls, in particular an external guide wall 16 that is curved, e.g. cylindrical, and against which the blister strip 20 slides. An internal guide wall 17 can also be provided at the inlet to the reception housing 15, and preferably extends approximately parallel to the external guide wall 16, so as to form a guide channel 18 for the blister strip 20. The guide walls 16, 17 further facilitate proper rolling up of the blister strip 20.

In the invention, at least one movable wall is provided so as to separate the storage housing 11 from the reception housing 15, said wall being displaced each time the device is actuated, so as to cause the volume of the reception housing 15 to increase progressively, and the volume of the storage housing 11 to decrease. Although the major portion of the blister strip 20 is initially disposed in the storage housing 11, said storage housing is going to empty progressively, whereas the reception housing 15 is going to fill up progressively with the portion of strip supporting the empty reservoirs. The invention thus makes it possible to optimize the volume that is available in the body 10. Advantageously, it is the blister strip itself that pushes said at least one movable wall, so as to displace it on each actuation.

Advantageously, the device includes a cassette forming a unit containing said blister strip 20, defining the storage and reception housings 11, 15, said at least one movable wall, and possibly the guide walls 16, 17. This embodiment makes it easier to assemble the blister strip 20 in the device.

FIGS. 1 and 2 show a first embodiment of the invention, in which the device includes a single movable wall 500 that is displaceable mainly in translation. The wall 500 that moves in translation advantageously includes two rounded or concave surfaces 501, 502 facing the storage housing 11 and the reception housing 15 respectively, so as to adapt to the blister strip 20 being rolled up. Lateral slide surfaces 503, 504 of the movable wall 500 are advantageously adapted to slide against respective complementary guide walls 553, 554. Advantageously, one or both guide walls 553, 554 can be curved a little, as shown in FIGS. 1 and 2, thereby causing the movable wall 500 to turn a little about its own axis while it is moving in translation. This makes it possible to optimize still further the volume that is available for the blister strip 20.

Figure 3:
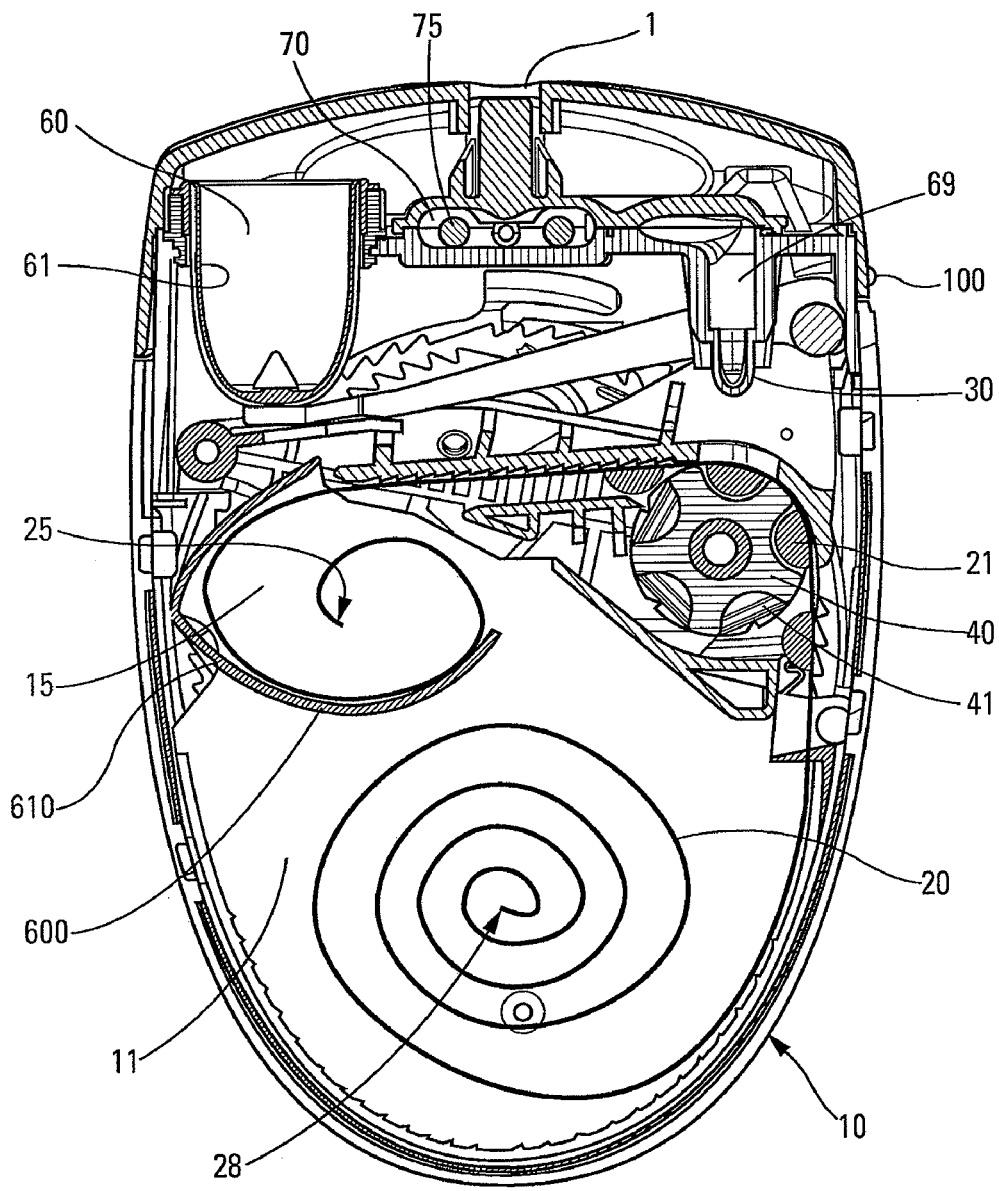
FIGS. 3 and 4 are diagrammatic section views of a dispenser device constituting another advantageous embodiment of the invention, respectively at the beginning and at the end of use of the device.
Figure 4:
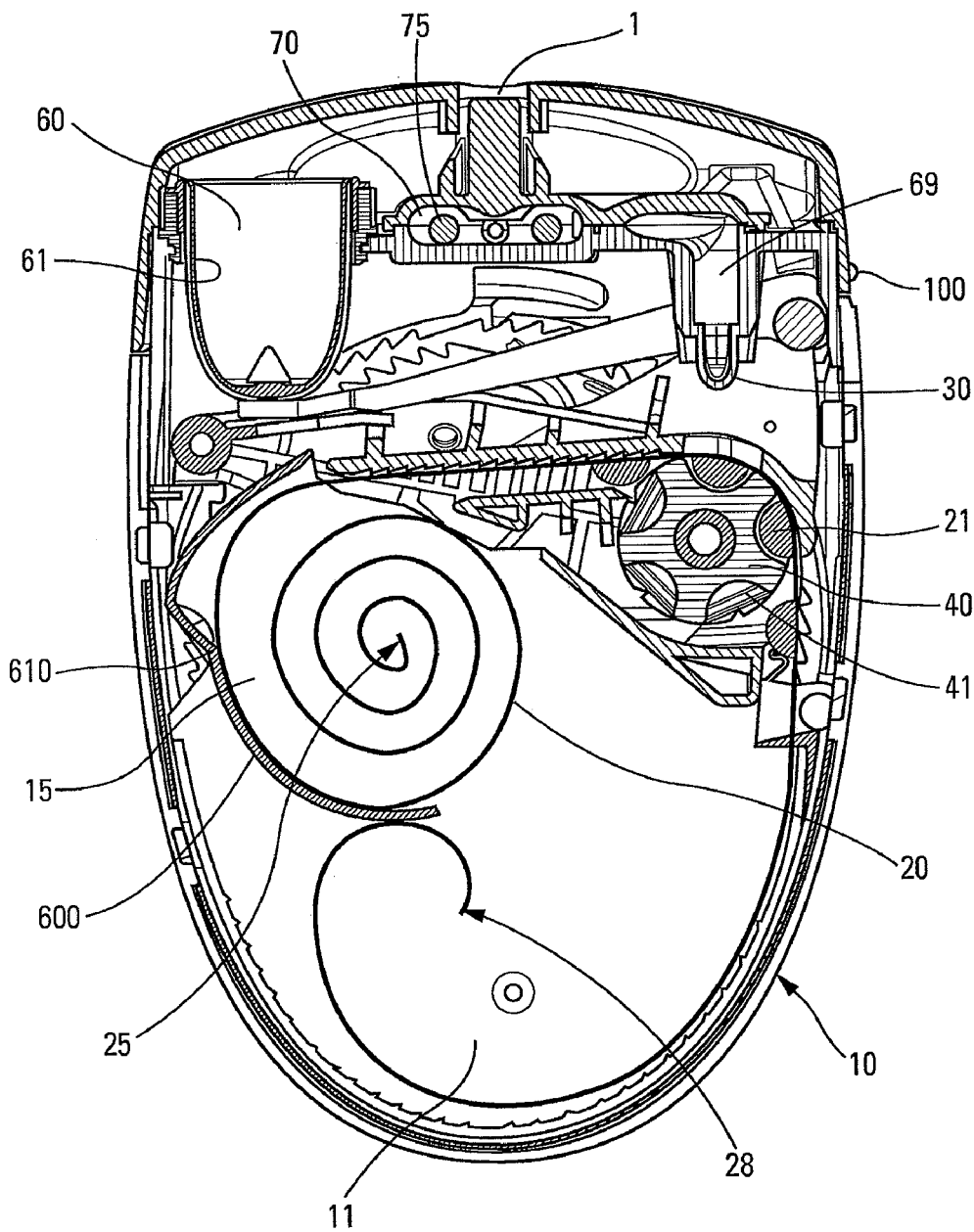

FIGS. 3 and 4 show a second embodiment of the invention in which there is a single movable pivot wall 600 that is advantageously rounded or concave relative to the reception housing 15 so as to adapt to the blister strip 20 being rolled up. The pivot wall 600 can pivot about a pivot point 610 that can be formed by a fold zone, as shown in FIGS. 3 and 4.

FIGS. 5 and 6 show another variant with two pivot walls 600, 601. In this embodiment, a second movable wall 601 is provided that is concave relative to the storage housing 11, the two walls 600, 601 sliding one on the other via their respective outside surfaces. Advantageously, each pivot wall 600, 601 can pivot about two pivot points 610 & 610' and 620 & 620' respectively. For each pivot wall, the two pivot points can be separated by a flexible connection piece, as shown in FIGS. 5 and 6. This enables the walls to pivot more easily, and makes it possible to optimize the available space.

The present invention therefore makes it possible to provide a dry-powder inhaler that performs the following functions in particular:

a plurality of individual doses of powder are stored in individual sealed reservoirs, e.g. 30 or 60 doses stored on a rolled-up strip;

the powder is released by perforation that is achieved by the user inhaling, the blister being perforated by means of an inhalation detector system that is coupled to a preprimed release system;

appropriately-shaped drive means are engaged with blisters so as to displace the blister strip on each actuation, and bring a new reservoir into a position in which it is to be opened by appropriate opening means; and safe, reliable, and compact storage is provided for the blister strip.

Other functions are also provided by the device of the invention as described above. It should be observed that the various functions, even if they are shown as being provided simultaneously on the various embodiments of the inhaler, could be implemented separately. En particular, the inhalation trigger mechanism could be used independently of the type of reservoir-opening means, independently of the use of a dose indicator, independently of the way in which the individual reservoirs are arranged relative to one another, etc. The prepriming means and the inhalation trigger system could be made in some other way. The same applies for other component parts of the device.

Various modifications can also be envisaged by a person skilled in the art, without going beyond the ambit of the present invention, as defined by the accompanying claims.

The invention claimed is:

1. A fluid dispenser device including a body (10) that is provided with a dispenser orifice (1), said body (10) containing a plurality of reservoirs (21) formed on a common substrate formed by an elongate strip (20) that includes a leading end (25) and a trailing end (28), the device further including reservoir-opening means (30) that are adapted to open a respective reservoir each time the device is actuated, and drive means (40) for driving the elongate strip (20), so as to bring a full reservoir into register with said opening means before, during or after each actuation of the device, said device comprising at least one movable wall (500; 600, 601) that separates, at least in part, a storage housing (11) for storing the elongate strip (20) from a reception housing (15) for receiving the elongate strip (20), said elongate strip (20) being disposed mainly in said storage housing (11) before the device is used for the first time, and being displaced progressively in said reception housing (15) each time the device is actuated, said at least one movable wall (500) causing the volume of the storage housing (11) to decrease progressively, and the volume of the reception housing (15) to increase progressively, said at least one movable wall including two pivot walls (600, 601) one of which (600) is concave relative to the reception housing (15) and the other one of which (601) is concave relative to the storage housing (11);

wherein the two pivot walls are displaced under the effect of a corresponding thrust exerted thereon by the elongate strip; and said two pivot walls slide one against the other while pivoting about a respective pivot, a free end of one of the two pivot walls extending generally toward the respective pivot of the other of the two pivot walls.

2. A device according to claim 1, in which said elongate strip (20) is disposed in a cassette that defines said storage and reception housing (11, 15) and that incorporates said at least one movable wall (500; 600, 601).

3. A device according to claim 1, in which said opening means (30) comprise a needle that does not move relative to the body (10), the respective reservoir (21) being displaced against said needle (30) each time the device is actuated, said needle (30) penetrating inside said respective reservoir (21) so as to empty said respective reservoir by an inhalation flow.

4. A device according to claim 1, in which said opening means (30) are actuated by the user inhaling, such that the reservoir is opened and emptied simultaneously by said inhalation flow.

5. The device according to claim 1, wherein said elongate strip is disposed rolled up in a roll mainly in said storage housing before the device is used for the first time.

6. A fluid dispenser device, comprising:
a body provided with a dispenser orifice;
a strip disposed in the body, the strip comprising a plurality of reservoirs between a leading end of the strip and a trailing end of the strip;
a perforator adapted to open a respective reservoir each time the device is actuated;
a drive wheel that drives the strip to bring an unopened reservoir into register with the perforator before, during or after each actuation of the device;
a storage housing for storing at least a portion of the strip having unopened reservoirs;
a reception housing for receiving at least a portion of the strip having opened reservoirs;
two movable walls that separate, at least in part, the storage housing from the reception housing, a first one of the two movable walls is concave relative to the storage housing and a second one of the two movable walls is concave relative to the reception housing;
the first of the two movable walls causing the volume of the storage housing to decrease progressively and the second of the two movable walls causing the volume of the reception housing to increase progressively as the strip is moved from the storage housing to the reception housing;
wherein the two movable walls are displaced under the effect of a corresponding thrust exerted thereon by the strip; and
wherein the two movable walls slide one against the other and rotate about respective pivot, a free end of one of the two movable walls extending generally toward the respective pivot of the other of the two movable walls.

7. The device according to claim 6, wherein the strip is disposed in a cassette that forms the storage and reception housing and that incorporates the two movable walls.

8. The device according to claim 6, wherein the perforator is a needle fixed relative to the body, the respective reservoir being displaced against the needle each time the device is actuated, the needle penetrating inside the respective reservoir so as to empty the respective reservoir by an inhalation flow.

9. The device according to claim 6, wherein opening of each reservoir is actuated by a user inhaling, such that the reservoir is opened and emptied simultaneously by flow of air caused by the inhaling.

10. The device according to claim 6, wherein all or most of the strip is rolled up in the storage housing before the device is used for the first time.